United States Patent [19]

Weissman et al.

[11] 4,388,924
[45] Jun. 21, 1983

[54] METHOD FOR LASER DEPILATION

[76] Inventors: Howard R. Weissman, 9216 Middlebelt, Livonia, Mich. 48150; Joseph Mantel, 21819 Constitution, Southfield, both of Mich. 48076

[21] Appl. No.: 265,878

[22] Filed: May 21, 1981

[51] Int. Cl.³ .............................................. A61N 5/00
[52] U.S. Cl. ................................. 128/303.1; 128/355; 128/398
[58] Field of Search ...................... 128/303.1, 395–398, 128/355

[56] References Cited

U.S. PATENT DOCUMENTS

| | | | |
|---|---|---|---|
| 3,538,919 | 11/1970 | Meyer | 128/398 |
| 3,653,384 | 4/1972 | Swope | 128/395 |
| 3,693,623 | 9/1972 | Harte et al. | 128/398 X |
| 3,720,213 | 3/1973 | Hobart | 128/395 |
| 3,834,391 | 9/1974 | Block | 128/398 X |
| 3,865,113 | 2/1975 | Sharon et al. | 128/325 |

FOREIGN PATENT DOCUMENTS 2260016 3/1974 Fed. Rep. of Germany ... 128/303.1
2827639 1/1979 Fed. Rep. of Germany ... 128/303.1

OTHER PUBLICATIONS

Liben et al., "An Argon Laser Photocoagulator", APL Tech. Digest, vol. 11, No. 3, Jan.-Feb. 1972, pp. 2–14.

Primary Examiner—Lee S. Cohen
Attorney, Agent, or Firm—Krass, Young & Schivley

[57] ABSTRACT

The roots of human hairs of a patient are devitalized using high intensity, short duration pulses of light having wavelengths with respect to which the skin of the patient is non-absorbative and the hair of the patient is relatively absorbative. A narrow, focused beam of the light is aimed at the epidermis of the patient adjacent the hair such that an extension of the beam intersects the hair root at an angle relative to the skin surface. A short pulse passes through the skin and is absorbed in the hair root, destroying its blood supply. Apparatus for practicing the method employs a manually controlled two-axis positioning system supporting the focusing system that is connected to a laser light source by a flexible fiber optic bundle. A shutter selectively positionable in the optical path allows a low intensity beam to be produced for aiming and the shutter is removed from the optical path for the pulse period to produce the high energy beam.

7 Claims, 4 Drawing Figures

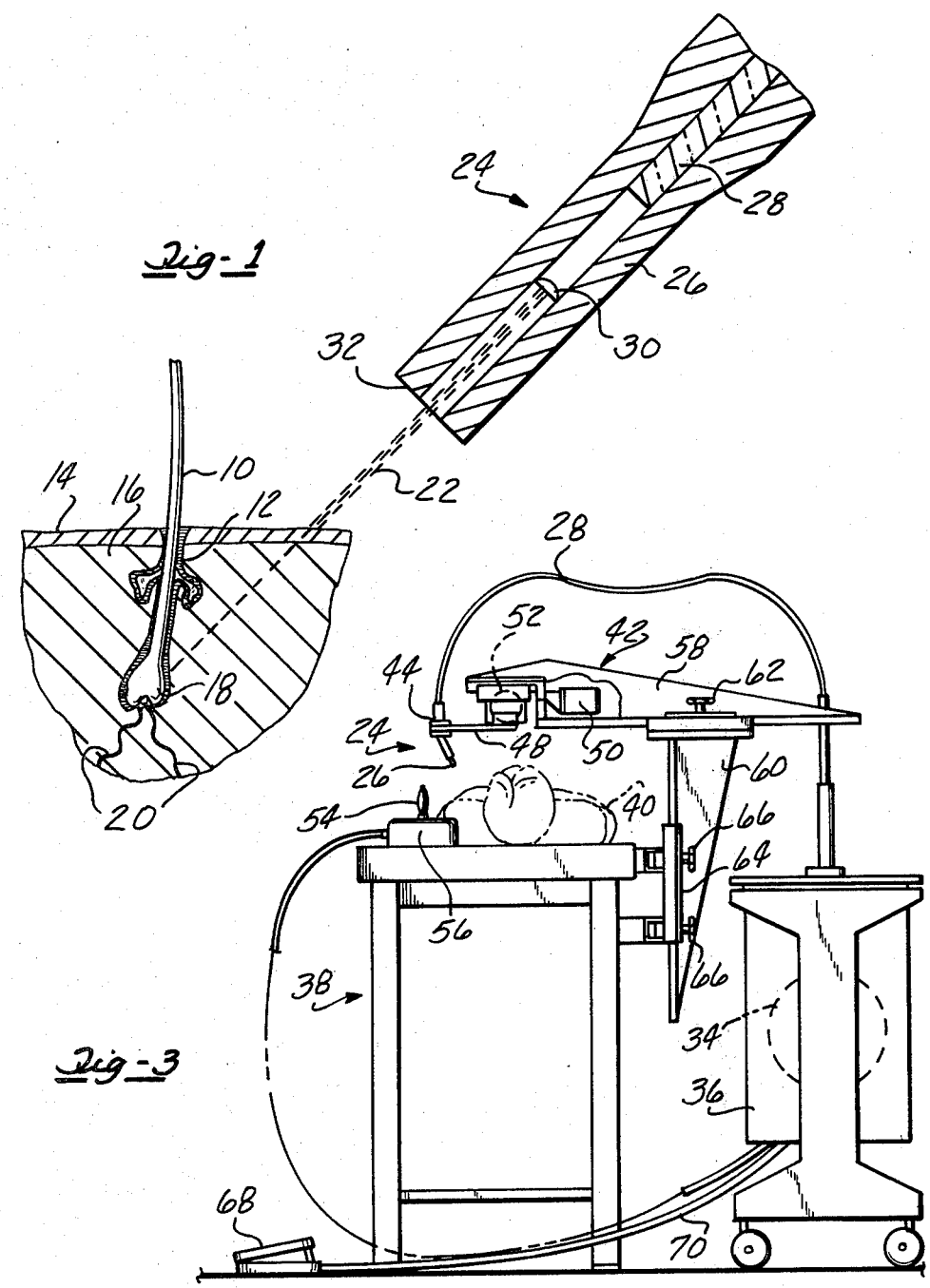

METHOD FOR LASER DEPILATION

DESCRIPTION

1. Technical Field

This invention relates to a method and apparatus for devitalization of human hair through use of a high energy, short duration, light pulse of a wavelength that passes through the skin of the patient without substantial absorption and is absorbed in the hair root.

2. Background Art

Relatively permanent removal of aesthetically undesirable body hair is generally performed on a clinical basis using electrolysis techniques. These techniques involve some pain, are time consuming, and demand a fair degree of expertise in their application.

As an alternative, it has been proposed to employ high energy light pulses to heat and thereby devitalize the blood circulation system which feeds the hair roots. U.S. Pat. No. 3,693,623 discloses a technique in which a high energy light pulse is derived from a Xenon arc source and passed through a glass fiber conduit to a manually supported probe terminating in an elongated single glass fiber needle adapted to be extended into a hair follicle, alongside the hair body. The high energy light pulse from the Xenon arc source is then passed through the conduit to cause photo-coagulation of body tissue surrounding the follicle, devitalizing the hair.

U.S. Pat. No. 3,834,391 suggests a number of disadvantages of the photo-coagulation method involving insertion of a fine optical fiber into the hair follicle and discloses an alternative method wherein the light pulse from the Xenon lamp is positioned " . . . to the exterior of and touching the entrance of a follicle containing a living hair shaft and root . . . " so that the light energy is transmitted through the oils contained with the follicle to heat the body tissues adjacent to the hair root to devitalize the hair. The latter patent proposes rubbing mineral oil into the epidermis in the vicinity of the follicle prior to applying the light pulse in order to assure the proper transmission of the light through the follicle.

This latter method involves extremely accurate positioning of the manually supported probe and depends upon the highly variable thermal conductivity of the hair follicle to achieve the goal.

DISCLOSURE OF THE INVENTION

The present invention relates to an improved method of photo-depilation and to apparatus for practicing the method which relieves the operator of the difficult task of manually positioning the probe with a high degree of precision, is substantially painless to the patient and devitalizes a higher percentage of body hairs operated upon than the previous method.

Broadly, the method of the present invention involves generating a focused, collimated pulse of light at a point on the epidermis of the patient closely separated from the exit point of the hair body and at an angle to the epidermis surface aimed at the hair root. The light pulse is of such a wavelength that there is very little absorption of the light within the epidermis and dermis of the patient but most of the light is absorbed within the hair root, causing heating of the hair root and coagulation of the tiny arteries which sustain life within the root. The method works best with relatively light skinned, dark haired patients—i.e., brunette Caucasians, whose body hair is the most visually apparent, but also works with varying degrees of efficacy with lighter haired and darker skinned patients. The wavelength of the light used is preferably in the vicinity of 5,000 angstroms and is preferably derived from an argon laser.

The use of a focused beam projecting from the end of a probe allows the probe to be supported a short distance away from the hair body, such as ½ to ¾ of an inch, so the operator has a clear field of vision as to the position of the probe and the beam relative to the hair and its root. The burden on the operator is further relieved through use of a novel apparatus which supports the probe end and allows it to be easily positioned within a two-axis coordinate system. The preferred embodiment of the positioning system includes a pair of pulse motors which drive the probe along two perpendicular coordinate axes. A manually controlled joy stick controls the generation of pulses that are provided to the two motors. The pulses for the two axes are generated as a function of the displacement and direction of displacement of the joy stick from its neutral position. Moving the joy stick in one direction provides pulses for one of the motors at a rate proportional to the displacement of the joy stick. Motion of the joy stick at 90° to that direction controls the other motor. Motions of the joy stick at intermediate angles produce motions which are functions of the x and y components of the joy stick motion.

In the practice of the method, the patient lies on a table and the probe support is adjusted so that the probe end is closely spaced above the area of the patient's skin to be operated upon. The motor driven control system is then used to accurately position the probe.

The optical system includes an attenuator normally positioned in the laser beam path so that the output beam is greatly reduced in intensity and enlarged in diameter and may be used to position the probe. When the desired probe position is achieved the attenuator is removed from the optical path for the desired pulse time, allowing passage of the full high energy pulse which produces the desired photo-coagulation. The pulses may be repeated until the hair body is easily removed from the follicle.

Other objectives, advantages and applications of the present invention will be made apparent by the following detailed description of the preferred embodiment of the method and apparatus.

BRIEF DESCRIPTION OF THE DRAWINGS

The description makes reference to the accompanying drawings in which:

FIG. 1 is a schematic view illustrating the beam output end of the optical system positioned above the skin of a patient in accordance with the inventive method to transmit thermal energy to the hair root to devitalize it, with the adjacent skin section of the patient shown in cross-section;

FIG. 3 is a side view of the apparatus of the present invention; and

DETAILED DESCRIPTION

Figure 4:
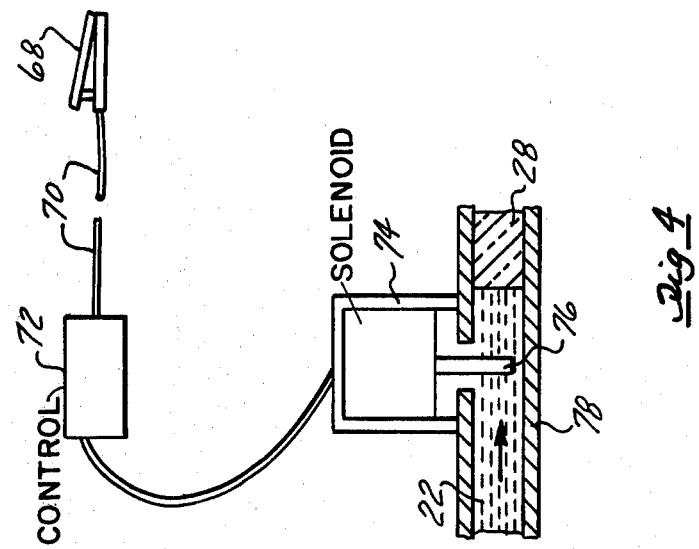
FIG. 4 is a schematic view of the beam attenuator.

A cross-section through a hair body 10 and the surrounding skin section is illustrated in FIG. 1. The hair body 10 is supported in a hair follicle or passage 12 formed through the surface epidermis 14 of the patient and the underlying dermis 16. At its lower end the hair body terminates in a root section 18 nourished by a network of small blood vessels 20. In order to remove the hair in such a manner as to prevent recurrent growth it is necessary to devitalize the root section 18 as by coagulating the vessels 20 to prevent nourishment of the root 18. In the practice of the present invention an intense collimated beam of light 22 is aimed at a point on the epidermis of the patient spaced from the exit point of the hair follicle through the epidermis, and at such an angle with respect to the epidermis so that a continuation of the beam intersects the hair root 18.

The beam will preferably have an actual strength of ½ to 2½ watts and may be derived from a laser having a maximum power of approximately 3 watts.

The beam will necessarily be projected for a relatively short duration; i.e., less than about 0.40 seconds, and preferably more than 0.01 seconds, depending in part upon the beam strength.

The beam will preferably be derived from an argon laser and will have most of its energy in the wavelength of approximately 4,800 to 5,200 angstroms. Light of this wavelength passes through relatively light human skin without any appreciable absorption yet is highly absorbed in a dark hair root. The thermal energy produced upon absorption of the light energy within the hair root 18 causes coagulation of the blood vessels 20 and destroys the hair root. The hair body is generally vaporized in this process. It may be necessary to apply multiple pulses to allow complete devitalization. This process is relatively painless to the patient because of the low degree of absorbency and short pulse within the dermis 16.

In order to allow careful aiming of the probe relative to the hair body before the power beam is applied, a light beam having only a small fraction of the power of the devitalizing beam is preferably employed. Such a lower power beam may be generated by blocking the major portion of the optical path from the laser by an attenuator in a manner which will be subsequently described. Since this aiming beam is derived from the same source and uses the same optical path as the devitalizing beam, it allows accurate positioning of the probe.

In FIG. 1, the probe, generally indicated at 24, comprises an elongated tube 26 supporting the output end of a flexible optical fiber bundle 28. A plano-convex lens 30 is positioned in the tube 26 with its convex surface in opposition to the end of the fiber optic bundle 28. The lens 30 collimates a beam of light emerging from the bundle 28 at a point a few millimeters beyond the tube end 32. Therefore the probe 24 may be positioned with its end a short distance above the skin of the patient to allow a clear field of view for aiming the laser.

Figure 2:
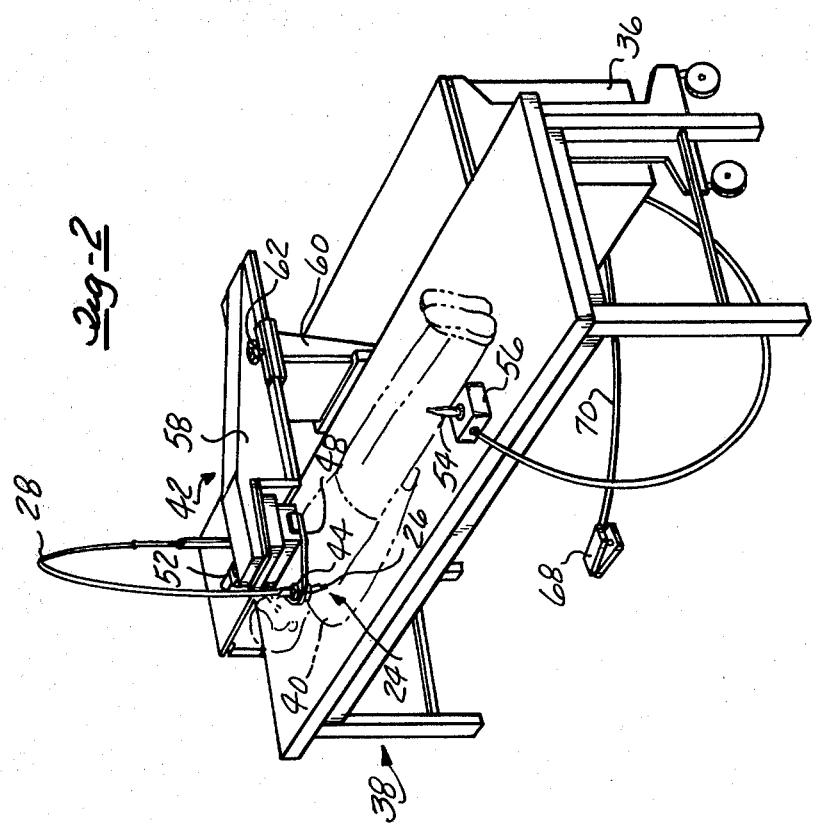
FIG. 2 is a perspective view of the apparatus of the present method being used to remove facial hair.

A preferred embodiment of apparatus for practicing the method of the present invention is illustrated in FIGS. 2 and 3. The apparatus broadly consists of a laser 34 supported within a wheeled table 36; an examination table, generally indicated at 38 on which a patient 40 may lie; and a positioning system 42 which supports and adjusts the probe end 24 of the optical system with respect to the examination table. In the preferred embodiment of the invention the laser 34, its supporting table 36, the optical fiber cable 28 and the probe 24, including the shutter system, may be of the type made commercially available as the "System 1000 Argon Surgical Laser" by Coherent Radiation, Inc., Medical Division, of Palo Alto, Calif. This form of surgical laser is marketed for use by dermatologists and the like for use in removal of cutaneous anomalies. This system produces both the aiming and power beams required for the practice of the present invention when a 3-watt argon laser is provided with the system.

In the apparatus of the present invention the output probe 26 is supported in a friction ball joint 44 so that the angle of the probe relative to the support may be manually adjusted. The ball joint is fixed at the end of a support plate 48 retained in an x-y positioning system arrayed parallel to the surface of table 38. The positioning system is controlled by a pair of stepping motors 50 and 52. Drive signals for the stepping motors are generated under control of a manually adjustable joy stick 54 which projects from a control box 56 supported on top of the examination table.

The joy stick is spring biased into an upright vertical position. It may be manually moved against the bias in any direction. A commercially available system (not illustrated) generates two electrical signals having frequencies proportional to the components of the displacement of the joy stick from its neutral position, along two perpendicular axes. For example, if the joy stick is moved in a forward direction, away from the operator, pulses will only be provided by one of the generators, at a frequency proportional to the displacement of the joy stick from its neutral position. A movement at 90° to the first direction will produce pulses from the other generator and intermediate positions will produce pulses from both generators proportional to the components of that displacement along the two axes. The generators produce pulses of an opposite sign when the joy stick is moved in a reverse direction.

These pulses are provided to the stepping motors 50 and 52 to cause them to move the support plate 48 and the probe 44 in a direction and a rate proportional to the joy stick displacement.

The positioning system is supported on a beam 58 which projects horizontally over the top of the examination table 38. The horizontal beam 58 is supported in a vertically extending beam 60 and the horizontal extension of the beam 58 and its angle of extension may be manually adjusted employing a locking mechanism 62. Similarly, the vertical beam 60 is retained in a clamping system 64 affixed to the rear of the examination table 38. Manually adjustable clamps 66 may be used to adjust the vertical extension of the beam 60 with respect to the table.

A foot pedal 68 connected to the laser support table 36 by cable 70, allows operator switching between the attenuated, low power aiming beam and the high power depilation beam. FIG. 4 illustrates in schematic form the manner of attenuating the beam. The cable 70 connects to a control box 72 which in turn connects to a solenoid 74. A shutter 76 is energized by the solenoid 74. The shutter is disposed in the optical path of the laser beam before it reaches the fiber optic cable 28. The solenoid 74 is supported on a tube 78 through which the laser beam passes. When the shutter 76 is extended it blocks the major portion of the laser beam, allowing only a small percentage of the laser light, such as about 5%, to pass into the fiber optic cable 28. This produces the low power aiming beam. When the foot pedal 68 is depressed, the control 72 sends a short timed pulse, having a period independent of the period of depression of the foot pedal 68, to the solenoid 74, withdrawing the shutter for the period of the required depilating pulse. The shutter 76 is spring biased toward its closed position so that it will retain this position in event of failure of the solenoid 74.

In operation, a patient 40 lies on the examination table 38 and the probe and its support are manually positioned over the skin area of the patient to be operated upon, by adjustment of the horizontal beam 58 and the vertical beam 60. The angle of the probe 26 with respect to the support is also adjusted by manipulation of the ball joint 44. The laser is then energized to produce the low power aiming beam. The operator visually positions the probe 24 with respect to a hair root in the manner illustrated in FIG. 1 and then depresses the foot pedal 68, producing the power beam for the required period. The beam passes substantially transparently through the dermis and epidermis of the patient and is absorbed in the hair root 18, causing coagulation of the feeder vessels 20. The hair may then be manually removed by pulling on it.

The control system of the laser includes means for adjusting the output power of the laser and the duration of the beam for adjustment to individual patients.

Having thus described my invention, I claim:

1. The method of devitalizing a hair of a human subject as part of a process of depilation, comprising: aiming a source of a narrow beam of light, the source having a substantial component of wavelength to which the skin of the patient is substantially non-absorbative and the hair root of the patient is substantially absorbative, at a point on the epidermis of the patient spaced from the exit point of the hair body and in a direction such that the extension of the beam would intersect the hair root, and applying a short, high-energy pulse of such light energy from such beam to cause sufficient heating of the hair root to destroy the blood vessels supplying the hair root.

2. The method of claim 1 in which the light energy source is an argon laser.

3. The method of claim 2 in which the light pulse has a duration of between 0.020 and 0.30 seconds.

4. The method of claim 1 in which the aiming is achieved by use of a relatively continuous beam of lower energy intensity and wider cross-section than said light pulse, said low intensity beam being projected along the same optical path as said light pulse.

5. The method of claim 4 in which the source of the light pulse and the lower energy aiming beam constitute a laser and a beam attenuator normally disposed in the optical path of the laser, which attenuator is removed from the path for the pulse duration to achieve said light pulse.

6. The method of claim 1 including the step of pulling on the section of a hair body which extends from the epidermis following the devitalization to achieve depilation.

7. The method of claim 1 in which the light pulse has a wavelength substantially at 5,000 angstroms.

* * * * *